(12) United States Patent
Wepfer

(10) Patent No.: US 10,179,159 B2
(45) Date of Patent: Jan. 15, 2019

(54) TOPICAL ANESTHETIC FORMULATION

(76) Inventor: Scott Wepfer, Birmingham, AL (US)

(*) Notice: Subject to any disclaimer, the term of this patent is extended or adjusted under 35 U.S.C. 154(b) by 1807 days.

(21) Appl. No.: 11/835,500

(22) Filed: Aug. 8, 2007

(65) Prior Publication Data

US 2007/0269393 A1    Nov. 22, 2007

Related U.S. Application Data

(63) Continuation-in-part of application No. 10/645,951, filed on Aug. 22, 2003, now abandoned, which is a continuation-in-part of application No. 10/111,241, filed as application No. PCT/US00/41451 on Oct. 23, 2000, now Pat. No. 7,273,887.

(60) Provisional application No. 60/161,155, filed on Oct. 22, 1999.

(51) Int. Cl.
| | |
|---|---|
| A61K 31/496 | (2006.01) |
| A61K 31/7048 | (2006.01) |
| A61K 31/7034 | (2006.01) |
| A61K 38/12 | (2006.01) |
| A61K 9/06 | (2006.01) |
| A61K 47/10 | (2017.01) |

(52) U.S. Cl.
CPC ............... *A61K 38/12* (2013.01); *A61K 9/06* (2013.01); *A61K 31/496* (2013.01); *A61K 31/7034* (2013.01); *A61K 31/7048* (2013.01); *A61K 47/10* (2013.01)

(58) Field of Classification Search
CPC .. A61K 31/167; A61K 31/245; A61K 31/135; A61K 31/24; A61K 31/137
USPC ................... 514/535, 536, 537, 626; 424/449
See application file for complete search history.

(56) References Cited

U.S. PATENT DOCUMENTS

| | | | | |
|---|---|---|---|---|
| 3,832,460 | A | 8/1974 | Kosti | 424/54 |
| 4,181,725 | A * | 1/1980 | Voorhees et al. | 514/297 |
| 4,808,410 | A | 2/1989 | Sorrentino et al. | 424/435 |
| 4,895,727 | A * | 1/1990 | Allen | 424/642 |
| 5,081,157 | A | 1/1992 | Pomerantz | 514/781 |
| 5,204,090 | A * | 4/1993 | Han | A61K 8/37 424/47 |
| 5,279,837 | A * | 1/1994 | Hill | 424/682 |
| 5,314,685 | A * | 5/1994 | Tyle et al. | 424/401 |
| 5,446,070 | A * | 8/1995 | Mantelle | 514/772.6 |
| 5,534,242 | A | 7/1996 | Henry | 424/45 |
| 5,585,398 | A | 12/1996 | Ernst | 514/537 |
| 5,900,249 | A | 5/1999 | Smith | 424/443 |
| 5,961,997 | A | 10/1999 | Swinehart | 424/401 |
| 6,217,852 | B1 * | 4/2001 | Gildenberg | A61K 8/27 424/401 |
| 6,295,469 | B1 | 9/2001 | Linkwitz et al. | 604/20 |
| RE37,727 | E * | 6/2002 | Hind | 424/402 |
| 6,528,086 | B2 | 3/2003 | Zhang | 424/449 |
| 6,638,981 | B2 * | 10/2003 | Williams et al. | 514/656 |
| 6,673,363 | B2 * | 1/2004 | Luo et al. | 424/449 |
| 6,894,078 | B2 * | 5/2005 | Castillo | 514/626 |
| 2002/0058068 | A1 * | 5/2002 | Houze et al. | 424/487 |
| 2009/0053290 | A1 * | 2/2009 | Sand et al. | 424/449 |

FOREIGN PATENT DOCUMENTS

AU    2002245932 B2    10/2002

OTHER PUBLICATIONS

Remington's Pharmaceutical Sciences, 17th Edition, p. 1792, under Patient counseling Information.*
Drug Facts and Comparisions, 1997, pp. 2973-2975.*
Censi et al. Permeation and skin retention of quercetin from microemulsions containing Transcutol P. Drug Development and Industrial Pharamcy, 2011, 1-6, Early Online, ISSN 0363-9045 print/ISSN 1520-5762 online.*
Vaida et al. Prolongation of lidocaine spinal anesthesia with phenylephrine. Anesthesia and Analgesia, 1986, vol. 65, No. 7, pp. 781-785.
Williams et al. Benzyl Alcohol Attenuates the Pain of Lidocaine Injections and Prolongs Anesthesia. J. Dermatol Surg Oncol. 1994 vol. 20, pp. 730-733.
Remington's Pharmaceutical Sciences, 17th Edition, 1985. p. 17920.

* cited by examiner

*Primary Examiner* — Jennifer M Kim
(74) *Attorney, Agent, or Firm* — Avery N. Goldstein; Blue Filament Law PLLC

(57) ABSTRACT

The topical medicament gel formulation of the present invention includes an anesthetic, an anti-microbial, an oxidant, a nutrient, a diuretic, an opioid, an anti-emetic, an anti-seizure drug, and a non-steroidal anti-inflammatory drug (NSAID), USP in a molecular, as opposed to a salt form, as the active ingredient. Additional constituents illustratively include a skin penetration enhancer and a gelling agent. This invention deals with problems commonly associated with topical application of local medicaments such as: slow onset of action; need for occlusion; and rapid loss of effect due to rapid systemic dispersion. The invention permits enhanced penetration of the medicament and thereby allows for a lesser total dosage of pharmaceutically active ingredient. The use of a lesser total dosage also decreases systemic toxicity.

6 Claims, No Drawings de_TOPICAL ANESTHETIC FORMULATION

CROSS-REFERENCE TO RELATED APPLICATIONS

This application is a continuation-in-part of U.S. application Ser. No. 10/645,951 filed Aug. 22, 2003, now pending, which is a continuation-in-part of U.S. application Ser. No. 10/111,241 filed Jul. 10, 2002, now pending, which is the U.S. National Phase of PCT Application No. PCT/US00/41451 filed Oct. 23, 2000, now abandoned, which claims priority of U.S. Application No. 60/161,155 filed Oct. 22, 1999.

FIELD OF THE INVENTION

The present invention generally relates to transdermal medicaments, and in particular to a fast acting transdermal medicament delivery for penetration through the stratum corneum into the deep epidermis/dermis and is especially well suited for local anesthesia.

BACKGROUND OF THE INVENTION

The use of topical or dermal medicaments has long been utilized in the practice of medicine. In particular, topical anesthetics are commonly administered prior to painful medical procedures such as injections, biopsies, and the application of laser energy for cutaneous procedures such as removal of hair, tattoos, telangiectasias, etc., minor superficial surgeries, and the like.

Several topical anesthetic formulations have been extensively used by the medical field to obtain local anesthesia. These products are known to be effective as topical anesthetics; however, a long onset time, which is the time between the administration of the topical anesthetic and the commencement of the anesthetic effect, are a common limitation of conventional topical anesthetics. To enhance skin penetration of conventional topical anesthetics, it is often recommended that skin having anesthetic applied thereto be covered with an occlusive dressing. Typically, the onset of action for conventional topical anesthetics varies over a range of time, for example from 30 to 90 minutes. This variability in length of onset time leads to delays in the commencement of medical procedures and, because of the very wide variation in onset time, can lead to the premature commencement of procedures and the infliction of unnecessary pain on the patient.

One particular topical anesthetic utilized to suppress or eliminate pain during such procedures is known by the trade name EMLA®. This product is known to be effective as a topical anesthetic; however, EMLA® has a very long onset time, which can range from 45 to 90 minutes and, in some instances, can take even longer. The variability in length of onset time leads to delays in the commencement of medical procedures and, because of the very wide variation in onset time, can lead to the premature commencement of procedures, thereby inflicting unnecessary pain on the patient. EMLA® must also be covered with an occlusive dressing to enhance penetration. Another disadvantage of EMLA® is that one of its two active ingredients, prilocaine, causes vasoconstriction, and so cannot be used before procedures such as IV placement, blood drawing and laser removal of telangiectasias. EMLA is also an opaque cream and as a result decreases the effectiveness of laser procedures.

Accordingly, it would be advantageous and desirable to develop a topically applied, transdermally delivered anesthetic formulation for use before painful procedures such as laser hair removal and skin resurfacing, giving injections, starting IVs, drawing blood, biopsies and minor superficial surgeries which has a more rapid onset time, has less variability in the onset time, does not require occlusion, does not interfere with laser energy penetration into the skin, does not cause vasoconstriction and lastly, permits enhanced penetration of the medicament and thereby allows for a lesser total dosage of pharmaceutically active ingredient. The use of a lesser total dosage thus decreases systemic toxicity. Such a formulation will have a much wider clinical application.

Thus, there exists a need for a vehicle to enhance the transdermal penetration of the active medicament into the deeper epidermis and dermis layers of the skin where the peripheral nerve endings lie, allowing for a fast onset of action. There further exists a need to control the epidermal penetration rate to preclude rapid loss of the active medicament to the systemic circulatory system. With the development of a superior vehicle for transdermal delivery, there also exists rapid onset delivery not only of topical anesthetics to the deeper epidermal and dermis layers, but broad classes of other therapeutics.

SUMMARY OF THE INVENTION

A gel formulation for transdermal active medicament delivery is provided that confronts the paradoxical requirement that a topically applied local medicament quickly penetrate through the stratum corneum into the deeper epidermal and dermal layers of the skin and produce a rapid onset of action, yet having slow penetration into the systemic circulation. Such a formulation would be characterized as "transdermal" as it is designed to carry the active ingredients through the stratum corneum into the deeper regions of the skin.

The transdermal active medicament illustratively includes an anesthetic, an anti-microbial, an anti-tumoral, a cancer preventative drug, an anti-fungal, an antiviral, a bleaching agent, a melanin blocking agent, a keratolytic or exfoliator agent, an oxidizing agent, a cellular nutrient, an opioid, an analgesic, an anticonvulsant, an antidepressant, an alpha-2 adrenergic agonist, an alpha-1 adrenergic antagonist, an antihistamine, a leukotriene inhibitor, a testosterone antagonist, a calcium channel blocker, a non-steroidal anti-inflammatory drug (NSAID), a muscle relaxant, an anti-inflammatory glucocorticoid steroid, a counter-irritant agent, a homeopathic agent, a wound-healing agent, or a sunscreen ultraviolet (UV) protectant.

A formulation medicament is typically present in a molecular base form, as opposed to a salt form. The gelled formulation is anhydrous and contains a skin penetration enhancer.

A process for producing a therapeutic effect of reducing a patient's sensation of pain includes the application of a therapeutically effective amount of a first medicament topical spray formulation to an area of a patient's skin, mucosal tissue, or other surface area. The first medicament formulation is anhydrous and includes a topical medicament compound and a skin penetration enhancer and a volatile cosolvent.

Alternatively or subsequently, a therapeutically effective amount of an anhydrous gel medicament formulation is administered to the same area. The anhydrous gel medicament is allowed to remain in contact with the subject area for a period of time sufficient to reduce pain sensation.

DETAILED DESCRIPTION OF THE PREFERRED EMBODIMENTS

The present invention provides a transdermal medicament formulation for topical administration to the surface of the skin with continued delivery of the active medicament into the deeper regions of the skin.

In use, a therapeutically effective amount of the transdermal medicament formulation of the present invention is applied to the skin of a patient or subject prior to and/or during a medical procedure to treat the patient or subject.

The terms "patient" and "subject" mean all animals including humans. Examples of non-human patients or subjects include cows, dogs, cats, goats, sheep, and pigs.

The term "treating" includes, but is not limited to, the application of the transdermal medicament to the skin of a patient to prevent or inhibit the sensation of pain, treat a disease state, relieve symptoms, deliver a nutrient or oxygenate in the vicinity or region of the application of the transdermal formulation.

A therapeutically effective amount is an amount of the transdermal medicament formulation of the present invention, that when administered to a patient or subject, ameliorates, eliminates and/or inhibits pain, treats a disease state, delivers a nutrient, relieves a symptom or oxygenates in the local region or vicinity of the application of the topical medicament of the present invention.

While the preferable dosage forms for transdermal administration of the formulation of the present invention are as a spray or gel, an inventive formulation is also readily compounded as a cream or ointment. The active components are admixed with a physiologically acceptable carrier and any preservatives, or buffers, as may be required. Dental formulations containing appropriate flavors and sweeteners are also contemplated as being within the scope of this invention. With the exception of a spray, the inventive formulations are generally defined as "gelled".

The transdermal medicament formulations of the present invention are optionally packaged in an ointment tube, unit of use foil pack, ointment jar, or other suitable delivery device and can be applied to the surface of the skin utilizing a cotton swab, gauze pad, or other suitable applicator.

While the salts of an active medicament ingredient are operative herein, the base or non-ionized form of a medicament is preferably used to enhance solubility in an anhydrous formulation and to more easily traverse the stratum corneum as compared to a salt.

As used herein "anhydrous" is defined to be devoid of water with water contents of less than 5% and preferably less than 1% being present.

An inventive formulation is anhydrous and uses an organic skin penetration enhancer to facilitate transdermal transport of the medicament. Skin penetration enhancers operative in an inventive formulation illustratively include at least one of biologically acceptable glycols, diglycols, polyglycols; alkyoxy $C_2$-$C_8$ alcohols and a compound of the formula

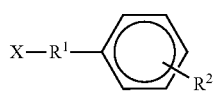

(I)

where $R^1$ is $C_1$-$C_6$ alkyl and $C_3$-$C_6$ alkylene; X is hydrogen, hydroxyl primary amine, alkyl, hydrogen and $R^2$ is hydrogen, $R^1$ or $R^1$—X with the proviso That at least one oxygen or nitrogen atom is present. Specific skin penetration enhancers operative herein are benzyl alcohol, 2-hydroxyethyl benzene, benzaldehyde, propylene glycol, and 2(2-ethoxyethoxy)ethanol. Preferably, the skin penetration enhancer is, or includes as a component, benzyl alcohol. A skin penetration enhancer is included at concentrations ranging from 5% to 95%, preferably 5% to 10% of the total weight of the gel composition.

Propylene glycol and 2-(2-ethoxyethoxy)ethanol are each individually typically present at concentrations of 0% to 90% of the total weight of the gel composition. A preferred range for each of these skin penetration enhancers is 10% to 60% of the total weight of the gel composition. Further preferred is a composition including one or both of these skin penetration enhancers at a concentration ranging from 25% to 45% of the total weight of the gel composition.

Benzyl alcohol is included in an inventive gel composition at concentrations ranging from 0% to 90% of the total weight of the gel composition, preferably 5% to 20%.

Compounds of Formula I have demonstrated an ability to solvate lipophilic (non-ionic) compounds and penetration of the stratum corneum. The high lipid solubility of the lidocaine base as well as that of the compounds of Formula I greatly diminish the need for a vasoconstrictor to be added to an inventive formulation to prolong the duration of anesthesia. This lipophilic nature of a base medicament and a skin penetration enhancer is seen as a positive quality since vasoconstrictors are contraindicated for many of the procedures that are indications for an inventive formulation, such as starting an IV and laser removal of telangiectasias.

The amphoteric properties of compounds of Formula I include strong lipophilicity and moderate hydrophilicity allowing compounds of Formula I to disrupt the highly structured lipid portion of the stratum corneum, or fluidizing stratum corneum lipids to facilitate lipid soluble medicament passage through the stratum corneum. Skin penetration enhancer lipophilicity is also believed to enhance the retention of lipophilic medicament in the subcutaneous tissues underlying the dermal site of application. This residence of the medicament in the deep dermis and epidermis increases the duration of local action and decreases systemic side effects by slowing continued medicament penetration into the systemic circulation.

A co-solvent is optionally used in an inventive gelled formulation and has the attribute of being more volatile to evaporation than the skin penetration enhancer. Anhydrous co-solvents operative herein illustratively include isopropyl alcohol, diethyl ether, and haloalkanes. Once applied to the skin, the co-solvent rapidly evaporates from the skin due to greater volatility. With volatilization of the co-solvent, the medicament is concentrated in the skin penetration enhancer which, due to its rapid skin permeation and good solvent characteristics, limits the deposition of medicament solutes on the skin surface. Typically, a co-solvent is present from 0 to 90% total weight percent of an inventive gel formulation.

It is also contemplated that the present invention can optionally include a vasoconstrictor which is utilized to retain a medicament longer at the application sites. Vasoconstrictors operative herein illustratively include phenylephrine, naphazoline, tetrahydrozoline, oxymetazoline, tramazoline, and salts thereof.

A transdermal small molecule active medicament delivered to the epidermis and deep dermis includes broad classes of lipophilic actives such as an anesthetic, an anti-microbial, an anti-tumoral, a cancer preventative drug, an anti-fungal, an antiviral, a bleaching agent, a melanin blocking agent, a keratolytic or exfoliator agent, an oxidizing agent, a cellular nutrient, an opioid, an analgesic, an anticonvulsant, an antidepressant, an alpha-2 adrenergic agonist, an alpha-1 adrenergic antagonist, an antihistamine, a leukotriene inhibitor, a testosterone antagonist, a calcium channel blocker, a non-steroidal anti-inflammatory drug anesthetic (NSAID), a muscle relaxant, an anti-inflammatory glucocorticoid steroid, a counter-irritant agent, a homeopathic agent, a wound-healing agent, a sunscreen UV protectant, and combinations of these. Preferably, the medicament is in base form, as compared to the more water soluble salt form.

An anesthetic operative herein illustratively includes lidocaine, pramoxine, bupivacaine, chloroprocaine, oxyprocaine, mepivacaine, piperocaine, tetracaine, procaine, dibucaine, benzocaine, and dyclocaine.

An antimicrobial operative herein illustratively includes penicillin, amoxicillin, ampicillin, azlocillin, bacampicillin, carbenicillin, cloxacillin, dicloxacillin, methicillin, mezlocillin, nafcillin, oxacillin, piperacillin, ticarcillin; cefepine, cefexime, cefotan, chlortetracycline, oxytetracycline, tetracycline, norfloxacin, itraconazole, imipenem, erythromycin, enoxacin, ofloxacin, pefloxacin, chloramphenicol, clofazimine, and dapsone; aminoglycosides such as streptomycin, neomycin and gentamicin; cephalosporins such as cephalothin, cefazolin, cephalexin, cefiroxime, cefamandole, cefoxitin and cefaclor; antibiotic glycopeptides such as vancomycin; lincosamides such as clindamycin; nitroimidazoles such as tinidazole and triclosan.

An anti-tumoral or cancer preventative drug operative herein illustratively includes 5-fluorouracil, iquimod, interferon and tretinoin.

An antifungal operative herein illustratively includes clotrimazole, miconazole, ketoconazole, fluconazole, amphotericin B, flucytosine, itraconazole, econazole, terbinafine, ciclopirox, faftifine, natamycin, griseofulvin, silver sulfadiazine, caspofungin, sertaconsazole, and tea tree oil.

An antiviral operative herein illustratively includes, 2-deoxy-D-glucose, acyclovir, famcyclovir, and valacyclovir.

A bleaching agent operative herein illustratively includes hydroquinone.

A melanin blocking agent operative herein illustratively includes kojic acid.

A keratolytic or exfoliator agent operative herein illustratively includes salicylic acid, retinoic acid and glycolic acid.

An oxidizing agent operative herein illustratively includes benzoyl peroxide and hydroquinone.

A cellular nutrient operative herein illustratively includes vitamins A, C, E, K and B complex, niacinamide, selenium, copper, magnesium, zinc, alpha lipoic acid, DMAE, hyaluronic acid and ubiquinone.

An opioid operative herein illustratively includes loperamide, fentanyl, meperidine, morphine, codeine, hydrocodone, hydromorphone, oxycodone and methadone.

A pain relieving drug operative herein illustratively includes tramadol and acetaminophen.

An anticonvulsant drug operative herein illustratively includes gabapentin, carbamazepine, pregabalin, phenytoin, clonazempam, divalproex sodium, lamotrigine, oxcarbazepine, tiagabine, valproic acid, and topiramate.

An antidepressant operative herein illustratively includes amitriptyline, amoxapine, desipramine, doxepin, imipramine, maprotiline, nortriptyline, protriptyline, trimipramine, phenelzine, tranylcypromine, isocarboxazid, fluoxetine, sertraline, fluvoxamine, paroxetine, citalopram, escitalopram, venlafaxine, mirtazepine, and bupropion.

An alpha-2 adrenergic agonist operative herein illustratively includes clonidine and tizanidine.

An alpha-1 adrenergic antagonist operative herein as doxazosin, prazosin and terazosin.

A beta adrenergic antagonist operative herein as acebutolol, atenolol, bisoprolol, metoprolol, nadolol, propranolol, and timolol.

An antihistamine operative herein illustratively includes for example, tranilast, alkylamines such as brompheniramine maleate, chlorpheniramine maleate and dexchlorpheniramine maleate; ethanolamines such as diphenhydramine HCl, carbinoxamine and clemastine fumarate; ethylenediamines, including pyrilamine maleate; phenothiazines such as promethazine HCl; piperidines such as cyproheptadine HCl; and other antihistamines such as the non-sedating compounds loratadine, fexofenadine and cetirizine.

A leukotriene inhibitor operative herein illustratively includes quercetin, montelukast, zafirlukast and zileuton.

A testosterone antagonist operative herein illustratively includes spironolactone.

A calcium channel blocker herein illustratively includes nisoldipine, nifedipine, nicardipine, bepridil, nimodipine, felodipine, amlodipine, diltiazem and verapamil.

A nonsteroidal anti-inflammatory drug (NSAID) operative herein illustratively includes celecoxib, ketoprofen, ketorolac, diflunisal, ibuprofen, nabumetone, piroxicam, naproxen, diclofenac, indomethacin, sulindac, tolmentin, etodolac and oxaprozin.

A muscle relaxant operative herein illustratively includes guiafenesin, cyclobenzaprine, carisoprodol, chlorzoxazone, diazepam, metaxalone, methocarbamol, orphenadrine, dantrolene and baclofen.

An anti-inflammatory glucocorticoid steroid operative herein illustratively includes hydrocortisone, betamethasone dipropionate, betamethasone valerate, clocortolone pivalate, desoximetasone, fluocinolone acetonide, flurandrenolide, fluticasone propionate, hydrocortisone butyrate, hydrocortisone valerate, memetasone furoate, triamcinolone acetonide, aclometasone dipropionate, desonide, dexamethasone, hydrocortisone acetate, amcinonide, diflorasone diacetate, fluocinonide, halcinonode, halobetasol propionate, clobetasol propionate and augmented betamethasone.

A counter-irritant agent operative herein illustratively includes camphor and menthol.

A homeopathic agent operative herein illustratively includes arnica, hypericum and rhus tox.

A wound healing agent operative herein illustratively includes phenytoin, allantoin and Misoprostal.

A sunscreen UV protectant operative herein illustratively includes oxybenzone, dioxybenzone, P-aminobenzoic acid, ethyl dihydroxy propyl PABA, octyl dimethyl PABA, glyceryl PABA, cinoxate, ethylhexyl p-methoxycinnamate, octocrylene, octyl methoxycinnamate, ethylhexyl salicylate, homosalate, oxtyl salicylate, methyl anthranilate, digalloyl trioleate, titanium dioxide and zinc oxide.

A transdermal macromolecular active medicament delivered to the epidermis and deep dermis includes polypeptides; proteins; nanocrystals; nanotubes; nucleic acids such as DNA, RNA, and small interfering RNA; dendrimers such as polylysine dendrimer, polyamidoamine dendrimer, polyproplyeimine dendrimer antivirals as detailed in AU2002245932; and combinations thereof. An exemplary combination is an antibody covalently bonded to or admixed with a nanocrystal. It is appreciated that localized protein transport can provide healing or therapeutic effects, as well as inducing an immune response akin to subcutaneous vaccination. Transdermal residence of a macromolecular active medicament provides benefits of localized labeling or marker insertion, selective transfection or therapy.

An inventive transdermal medicament gel formulation includes a gelling agent compatible with the inventive formulation components. For example, cellulose polymers are compatible with components of an inventive formulation. A preferred gelling agent is hydroxypropyl cellulose. Hydroxypropyl cellulose is generally available in grades ranging from about 5 cps to about 25000 cps. Generally hydroxypropyl cellulose ranging in viscosity from 500 cps to about 5000 at room temperature is included in an inventive composition at a final concentration ranging from about 0.2% to about 5%. Preferably, hydroxypropyl cellulose 1500 cps is included at a final concentration ranging from 1% to 3% of the total weight of the gel formulation.

Further optionally included in the inventive gel formulation is a humectant with emollient properties. An exemplary humectant includes glycerin. A humectant is included at concentrations ranging from 0 to 40%, preferably 5% to 25% of the total weight of the gel composition.

A preservative is optionally included in an inventive composition at a concentration effective to inhibit undesirable effects such as microbial growth, UV and/or oxygen-induced breakdown of composition components, and the like. A preservative operative in an inventive gel is any of those known in the art and compatible with the components of an inventive composition. Examples include butylated hydroxytoluene (BHT) used as an antioxidant and edetate disodium (EDTA) used as an antioxidant synergist. When a preservative is included, it is present at concentrations sufficient to confer a preservative effect. In the case of BHT the typical range is from 0.01 to 0.03% and in the case of EDTA the typical range is from 0.005 to 0.1%.

A fragrance is optionally added which may have the effect of pleasing and soothing the patient. An included fragrance is chosen which is compatible with the composition components. Menthol is an example of a suitable fragrance.

Other optional ingredients include, but are not limited to, a skin soothing agent, a coloring agent, a buffering agent, a film forming agent, and an opacifying agent and a combination of any of these or other components known in the art to be typical in transdermal formulations. The total concentration of such "other" agents generally ranges between 0% and 20% of the total weight of the composition.

TABLE I

Typical Composition Ranges for Inventive Transdermal Gel in Total Weight Percent of the Formulation

| Agent | Representative Component | Typical Range Values | Preferred Range |
|---|---|---|---|
| Small molecule Medicament (total) | lidocaine | 1-10 | 2-6 |
| Macromolecular Medicament (total) | collagen bonded to 5 nm Au nanocrystal | 0.001-1 | 0.01-0.5 |
| Skin Penetration Enhancer (total) | benzyl alcohol | 5-20 | 5-10 |
| | propylene glycol | 0-95 | 5-10 |
| | 2, (2-ethoxyethoxy)-ethanol | 0-95 | 25-45 |
| Gelling agent (total) | hydroxypropyl-cellulose | 0.2-5 | 1-2 |
| Humectant/Emollient (total) | glycerin | 0-40 | 5-25 |
| Preservative(total) | BHT | 0.02-0.5 | 0.03-0.1 |
| | EDTA | 0.01-0.1 | 0.03-0.07 |

TABLE I-continued

Typical Composition Ranges for Inventive Transdermal Gel in Total Weight Percent of the Formulation

| Agent | Representative Component | Typical Range Values | Preferred Range |
|---|---|---|---|
| Fragrance | menthol | 0-3 | 0.05-1 |
| Other | | 0-20 | 0.05-10 |

A gel formulation of a topical medicament according to the present invention is used separately or in conjunction with a spray anesthetic formulation.

Used separately, a gel formulation is applied to the area of the patient to be treated or otherwise affected. Generally, a pain-relieving or pain-reducing medicament effect is apparent within five minutes.

An exemplary gelled formulation includes an antibiotic selected from the group polymyxin B sulfate, bacitracin zinc and neomycin sulfate and combinations thereof. An antibiotic selected from this group is included at an appropriate dosage, for example, polymyxin B sulfate may range in amount from 1000-50000 units per gram of formulation, bacitracin zinc may range in amount from 100-5000 units per gram of formulation and neomycin sulfate may be added in amounts equivalent to about 1-25 milligrams of neomycin base per gram of formulation. A suitable mixture of antibiotics is illustrated by the combination of polymyxin B sulfate—10000 units per gram of gel formulation, bacitracin zinc—500 units per gram of gel formulation and neomycin sulfate equivalent to about 3.5 mg of neomycin base per gram of gel formulation. Other antibiotic formulations, combinations and concentrations may be included in a gelled formulation as appropriate for the therapeutic application.

An inventive transdermal composition of the present invention may be in a gelled form. A preferred gel formation is an anhydrous preparation that includes a topical medicament compound, a skin penetration enhancer, a co-solvent and a gelling agent. However, it is appreciated that a spray formulation is also well suited for transdermal medicament delivery to the epidermis. A representative spray formulation is provided in Table II.

TABLE II

Typical Composition Ranges for Inventive Transdermal Anesthetic Medicament Spray in Total Weight Percent of the Formulation

| Agent | Representative Component | Typical Range Values as percentage | Preferred Range as percentage |
|---|---|---|---|
| Small Molecular Medicament (total) | Lidocaine | 2-10 | 4-8 |
| Skin Penetration Enhancer (total) | benzyl alcohol | 0-35 | 5-21 |
| | propylene glycol | 0-40 | 1-10 |
| VOC Co-solvent (total) | Isopropyl alcohol | 40-99 | 70-90 |
| Antioxidant (total) | BHT | 0.02-0.5 | 0.03-0.1 |
| Preservative | EDTA | 0.01-0.1 | 0.03-0.07 |

An inventive formulation as described herein optionally contains a first medicament in conjunction with an antihistamine or anti-itch agent to provide added comfort, where anti-itch agents include cooling and soothing compounds such as camphor, thymol, calamine and crotamiton. An exemplary formulation of such contains a first medicament such as an anesthetic and an anti-itch agent of an alkylamine at a concentration ranging from 0.5-10% of the total weight of the formulation. A preferred formulation contains an alkylamine in amounts ranging from 0.75-3% of the total weight of the formulation. A specific formulation contains 0.5-5% diphenylhydramine hydrochloride.

In formulating an inventive composition containing both an anesthetic agent and an anti-itch agent, the anti-itch agent may be added to the mixture at the same time as the first medicament. In order to adjust the total volume to accommodate the volume of the anti-itch agent, the volume of one of the other ingredients is lowered. Typically, the volume of one or more of the skin penetration enhancers is lowered in an amount equal to the volume of the anti-itch ingredient. However, as will be evident to one of skill in the art, the volume of one or more of the other ingredients may be lowered in order to include the anti-itch agent at a desirable concentration.

In combination with another topical medicament formulation, a synergistic effect is achieved. In this embodiment it is preferred to use a liquid medicament formulation as detailed in Table II in conjunction with an anesthetic/anti-itch gel formulation as described herein. In a first step, a therapeutically effective amount of an inventive liquid medicament formulation is applied to an area of the patient to be anesthetized. Preferably, the liquid medicament formulation is applied as a spray, although other forms of application such as gelled will be recognized as operable in an inventive method. Following application of a liquid medicament formulation, a therapeutically effective amount of a gel anesthetic/anti-itch formulation is applied to the same area. The applied formulations are allowed to act for a period of time sufficient to achieve the desired level of anesthesia and/or anti-itch effect. The level of anesthesia may be determined by any of various methods known in the art, including patient report in response to painful stimulus. Similarly, anti-itch effect is generally gauged by patient report of effectiveness.

In combination with another topical medicament formulation, a synergistic effect is achieved. In this embodiment it is preferred to use a liquid anesthetic spray formulation as detailed in Table II in conjunction with an anesthetic gel formulation as detailed in Table I. In a first step, a therapeutically effective amount of an inventive liquid medicament formulation is applied to an area of the patient to be anesthetized. Preferably, the liquid anesthetic formulation is applied as a spray, although other forms of application will be recognized as operable in an inventive method. Following application of a liquid anesthetic formulation, a therapeutically effective amount of a gel anesthetic formulation is applied to the same area. The anesthetic formulations are allowed to act for a period of time sufficient to achieve the desired level of anesthesia. The level of anesthesia may be determined by any of various methods known in the art, including patient report in response to painful stimulus.

While the use of the transdermal anesthetic formulation of the present invention has been described for use in the laser removal of hair, applicant contemplates other uses including use prior to laser skin resurfacing and other cutaneous laser procedures, use prior to injection or insertion of an intravenous needle such as for the initiation of an intravenous drip, use prior to other types of needle sticks such as IM injections, inoculations and blood drawing, or other suitable uses for transdermal anesthesia which are well known to those skilled in the art.

The present invention is further detailed with respect to the following nonlimiting examples. These examples provide specific formulations but are not intended to limit the inventive scope as defined by the appended claims.

EXAMPLES

Example 1

Base Gel Formulation—Total Weight 100 gm

Benzyl alcohol, USP 10 gm
Isopropyl alcohol 84 gm
Hydroxypropyl cellulose 1500 cps 2 gm
Notes: Can add or subtract hydroxypropyl cellulose to obtain desired thickness.
1. Measure out benzyl alcohol and isopropyl alcohol and transfer into beaker other suitable mixing container. Add stir bar.
2. Weigh out hydroxypropyl cellulose 1500 cps and slowly sift through 40-mesh sieve into above mix with constant stirring by placing on stir plate.
3. Cover with plastic wrap to prevent evaporation during mixing.
4. Continue to stir above mix for at least 12 hours or until a uniform, clear gel has formed.

Example 2

Base Gel Formulation—Total Weight 100 gm

Propylene glycol, USP 10 gm
2-(2-ethoxyethoxy)ethanol 57.9 gm
Benzyl alcohol, USP 10 gm
Glycerin, USP 20 gm
Hydroxypropyl cellulose 1500 cps 2 gm
Menthol 0.1 gm (100 mg)
Notes: Can add or subtract hydroxypropyl cellulose to obtain desired thickness.
Following is the Specific Gravity (gm/ml) of the liquid ingredients used in the formulas above:
Propylene glycol, USP 1.037
2,2'-Ethoxyethoxyethanol 0.989
Benzyl alcohol, USP 1.045
Glycerin, USP 1.249
1. Measure out benzyl alcohol, propylene glycol, 2-(2-ethyoxyethoxy)ethanol and glycerin and transfer into beaker or other suitable mixing container.
2. Weigh out hydroxypropyl cellulose 1500 cps and slowly sift through 40-mesh sieve into above with constant stirring.
3. Continue to stir above mix for at least 12 hours or until a uniform, clear gel has formed.

Example 3

100 gm of Gel Anesthetic

Benzyl alcohol 10.0 gm (10 ml) (Specific gravity 1.045)
Lidocaine, USP (base) 4 gm
Menthol, USP 0.1 gm
Butylated hydroxytoluene, NF (BHT) 0.05 gm
Propylene glycol, USP 10 gm (9.65 ml) (Specific gravity=1.036)
2-(2-ethoxyethoxy)ethanol 54.8 gm (55.4 ml) (Specific gravity=0.989)
EDTA Disodium, USP 0.05 gm
Glycerin, USP 99.5% Anhydrous 20 gm (16 ml) (Specific gravity=1.249)
Hydroxypropyl cellulose, NF 1500 cps 1 gm
Notes: Can add or subtract hydroxypropyl cellulose to obtain desired thickness.

1. Measure out benzyl alcohol into mixing container.
2. Dissolve lidocaine, menthol and BHT in benzyl alcohol.
3. Measure out propylene glycol and ethoxydiglycol.
4. Dissolve EDTA disodium in #3. (This takes several minutes of constant stirring.)
5. Measure out glycerin and add to mixture when disodium edetate is completely dissolved.
6. Add #5 to #2.
7. Measure out hydroxypropyl cellulose 1500 cps and slowly add through a 40-mesh sieve into the mixture resulting from step #5 while constantly stirring mixture.
8. Stir until hydroxypropyl cellulose has uniformly gelled (usually needs to stir overnight).

Example 4

100 gm of Gel Antibiotic

Polymyxin B sulfate 10000 units per gm
Bacitracin zinc 500 units per gm
Neomycin sulfate equivalent to 3.5 mg of neomycin base per gm Butylated hydroxytoluene, NF (BHT) 0.05 gm
Propylene glycol, USP 35 gm (33.784 ml) (Specific gravity=1.036)
Diethylene glycol monoethyl ether, reagent 35 gm (35.389 ml) (Specific gravity=0.989)
EDTA Disodium, USP 0.05 gm
Glycerin, USP 99.5% Anhydrous 14.8 gm (11.849 ml) (Specific gravity=1.249)
Hydroxypropyl cellulose, NF 1500 cps 1 gm
Skin penetration enhancers and/or "other" ingredients to 100 g.

Example 5

| Anesthetic Spray Formulation - Total Weight 100 gm | | |
| --- | --- | --- |
| Lidocaine, USP | 4.0 gm | (active ingredient) |
| Benzyl alcohol | 10.0 ml | (penetration enhancer) |
| Isopropyl alcohol | ml gm | (co-solvent) |

Mixing instructions:
1. Weigh out lidocaine.
2. Transfer to 100 ml beaker.
3. Place beaker on stir plate.
4. Add benzyl alcohol and stir bar.
5. Cover with plastic wrap while spinning to prevent evaporation.
6. Stir until dissolved.
7. Next add isopropyl alcohol.
8. Cover with plastic wrap while spinning to prevent evaporation.
9. Stir until well mixed.
10. Dispense in a spray bottle.

Example 6

Anesthetic Effect

The formulation according to the present invention is found to be 100% effective in preventing any discomfort associated with the laser removal of hair using an Alexandrite Laser in twelve of twelve patients. In six of these instances, the procedure had been previously done once before utilizing EMLA® gel which was applied approximately ninety minutes prior to the initiation of the laser hair removal. In these six patients, their procedures had to be stopped prematurely due to patient discomfort. When the patients were re-lasered after pretreating with the transdermal pain formulation of Example 3, none of these six patients reported any discomfort from the second procedure which was completed. One of the twelve patients or subjects was a male who had hair removed from his back, a laser hair removal procedure recognized to be one of the most painful.

A commercial kit is provided by the present invention which includes a gelled formulation containing a medicament as described herein, along with instructions for use thereof for use in transdermal delivery. A spray formulation of the present invention that has the same or different medicament as the gelled formulation is also optionally provided in the kit so as to provide a synergistic rapid spray onset and a more prolonged gelled formulation delivery.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

It is appreciated that a variety of skin penetration enhancers, skin compatible and medicament solvating co-solvents and bases in addition to those detailed herein are known to one skilled in the art. Skin penetration enhancers additionally operative here in place of or in combination with those of Table I illustratively include 2-(2-ethoxyethoxy)ethanol, propylene glycol and those detailed in "Percutaneous Penetration Enhancers: The Fundamentals," E. W. Smith and H. I. Maibach, July 1999, pp. 1-512, which is incorporated herein by reference.

In view of the teaching presented herein, other modifications and variations of the present invention will readily be apparent to those of skill in the art. The discussion and description are illustrative of some embodiments of the present invention, but are not meant to be limitations on the practice thereof. It is the following claims, including all equivalents, which define the scope of the invention.

The invention claimed is:
1. A gelled formulation consisting of:
   a sunscreen UV protectant present up to 10 total weight percent;
   a gelled anhydrous base formed from a gelling agent;
   a skin penetration enhancer in said gelled anhydrous base and selected from the group consisting of: 2-(2-ethoxyethoxy)ethanol alone, or in combination with propylene glycol present in an amount from 1 to 10 total weight percent, or benzyl alcohol; and
   wherein said 2-(2-ethoxyethoxy)ethanol is present from at least 25 total weight percent, said sunscreen UV protectant being soluble in said skin penetration enhancer.
2. The formulation of claim 1 wherein said sunscreen UV protectant is at least one of oxybenzone, dioxybenzone, P-aminobenzoic acid, ethyl dihydroxy propyl PABA, octyl dimethyl PABA, glyceryl PABA, cinoxate, ethylhexyl p-methoxycinnamate, octocrylene, octyl methoxycinnamate, ethylhexyl salicylate, homosalate, oxtyl salicylate, methyl anthranilate, or digalloyl trioleate.
3. The formulation of claim 1 wherein said skin penetration enhancer is present from 25 to 45 total weight percent.
4. The formulation of claim 1 wherein the gelling agent is a cellulosic polymer.

5. The formulation of claim 1 wherein said gelling agent is hydroxypropyl cellulose.

6. A gelled formulation consisting of:
- a sunscreen UV protectant present up to 10 total weight percent;
- a gelled anhydrous base formed from a gelling agent;
- a skin penetration enhancer in said gelled anhydrous base and selected from the group consisting of: 2-(2-ethoxyethoxy)ethanol alone or in combination with propylene glycol present in an amount from 1 to 10 total weight percent, or benzyl alcohol; and
- at least one ingredient selected from the group consisting of: a preservative, a fragrance, a buffer, and an emollient;
- wherein said 2-(2-ethoxyethoxy)ethanol is present from at least 25 total weight percent, said sunscreen UV protectant being soluble in said skin penetration enhancer.

\* \* \* \* \*